US 6,719,839 B2

(12) United States Patent
Isager et al.

(10) Patent No.: US 6,719,839 B2
(45) Date of Patent: Apr. 13, 2004

(54) WATER DISPERSIBLE COMPOSITIONS CONTAINING NATURAL HYDROPHILIC WATER-INSOLUBLE PIGMENTS, METHODS OF PREPARING SAME AND THEIR USE

(75) Inventors: Per Pihlmann Isager, Milwaukee, WI (US); Marianne Winning, Kokkedal (DK)

(73) Assignee: CHR. Hansen A/S, Hoersholm (DK)

( * ) Notice: Subject to any disclaimer, the term of this patent is extended or adjusted under 35 U.S.C. 154(b) by 0 days.

(21) Appl. No.: 10/222,818

(22) Filed: Aug. 19, 2002

(65) Prior Publication Data

US 2003/0041780 A1 Mar. 6, 2003

Related U.S. Application Data

(63) Continuation of application No. 09/101,764, filed as application No. PCT/DK97/00026 on Jan. 20, 1997, now abandoned.

(30) Foreign Application Priority Data

Jan. 22, 1996 (EP) .............................. 96610003

(51) Int. Cl.[7] .............................. C08K 9/04; A61K 9/10; A23L 1/275
(52) U.S. Cl. .................... 106/501.1; 106/402; 106/471; 106/493; 106/498; 424/439; 424/499; 426/250
(58) Field of Search ................................ 106/402, 471, 106/493, 498, 501.1; 424/439, 499; 426/250

(56) References Cited

U.S. PATENT DOCUMENTS

| 4,475,919 A | 10/1984 | Woznicki et al. |
| 5,460,823 A | 10/1995 | Jensen et al. |
| 6,007,856 A | * 12/1999 | Cox et al. .................... 426/250 |
| 6,093,348 A | * 7/2000 | Kowalski et al. ........ 252/363.5 |

FOREIGN PATENT DOCUMENTS

| DE | 28 20 981 | 4/1979 |
| EP | 0 025 637 B1 | 5/1984 |
| EP | 0 498 824 | 1/1994 |
| JP | 6-172170 A | 6/1994 |
| JP | 7-90188 A | 4/1995 |
| WO | 91/06292 | 5/1991 |
| WO | 92/11002 | 7/1992 |

OTHER PUBLICATIONS

I. Smith, Natural Food Colorants, second edition (1991) pp. 169–201, no month provided.

* cited by examiner

*Primary Examiner*—David Brunsman
(74) *Attorney, Agent, or Firm*—Foley & Lardner

(57) ABSTRACT

Ready-to-use water dispersible pigment compositions containing waer-insoluble, hydrophilic pigments are provided. The compositions comprise a stable dispersion of the pigment such as a porphyrin pigment, carmine, curcumin and a carotenoid in the form of bodies of an average size which is at the most 10 μm is provided. The pigment bodies are dispersed without the use of a surface active substance in an aqueous phase comprising a hydrocolloid. The natural pigment compositions which are useful for coloring of food products and pharmaceuticals do not migrate in the products and they are acid stable. The compositions are useful in coating compositions for tablets and dragees.

28 Claims, No Drawings

US 6,719,839 B2

WATER DISPERSIBLE COMPOSITIONS CONTAINING NATURAL HYDROPHILIC WATER-INSOLUBLE PIGMENTS, METHODS OF PREPARING SAME AND THEIR USE

This is a Continuation Application of Application No. 09/101,764, filed Sep. 21, 1998, now abandoned, which is the U.S. national stage of PCT/DK97/0026, filed Jan. 20, 1997.

FIELD OF INVENTION

The present invention provides ready-to-use water dispersible compositions containing natural hydrophilic, water-insoluble pigments which are useful for the colouring of edible products and pharmaceutical products.

TECHNICAL BACKGROUND AND PRIOR ART

Colouring agents are commonly used as additives in the manufacturing of food products and pharmaceuticals. A wide range of such colouring agents are commercially available making it possible, when a particular colour tone is desired, to select a single agent having the desired colour or a mixture of agents which in an appropriate combination impart the desired colour to the product.

The commercial colouring agents can be synthetic substances which are also normally referred to as dyes or azodyes, or the agents can be pigments of natural origin, e.g. in the form of plant material containing the pigment or as more or less purified pigments extracted from plants, animals or microorganisms.

Occasionally, food grade or pharmaceutically acceptable colouring agents are provided in the form of synthetic or artificial substances having the same chemical composition as naturally occurring pigments. This type of colouring agents are also referred to in the art as "nature identical" colours. However, in the present context the term "natural pigment" is used exclusively to designate pigments which are derived from a natural source.

Food grade or pharmaceutically acceptable natural pigments can be water soluble or they can be essentially water-insoluble or sparingly soluble in water, including hydrophobic pigments. A water soluble natural pigment as such can only be used for colouring a product having an aqueous phase during and/or after manufacturing. Similarly, the use of a hydrophobic natural pigment as such requires that the product to be coloured has a lipid phase in which the pigment is soluble.

Certain pigments of natural origin such as metal chelates of carminic acid and curcumin, norbixin and chlorophyllin are insoluble in water at neutral pH or below but soluble in alkaline solutions. In this context, the term "natural hydrophilic water-insoluble pigment", refers to pigments of natural origin which are generally insoluble in aqueous media at about neutral pH or below but soluble in aqueous media at pH values in the alkaline range. Accordingly, the natural hydrophilic water-insoluble pigments which are dissolved in alkaline media precipitate at a pH level below 7.

However, it may be desirable to obtain the colour tone of a particular water-insoluble, hydrophilic natural pigment or a mixture of such pigments in a food product or a pharmaceutical product which does not comprise a phase in which the pigment is readily soluble, e.g. an aqueous phase with a pH value below 7. There is therefore an industrial need for colouring agents containing water-insoluble, hydrophilic natural pigments in the form of acid-proof water-miscible or water dispersible compositions.

Commercial water dispersible preparations of water-insoluble natural pigments such as carmine are e.g. available from Overseal Foods Ltd, Derbyshire, England under the trade name miChroma™. These products are provided as suspensions in propylene glycol and glucose syrup and the manufacturer states in data sheets that the products will stain clothing and skin.

In the pharmaceutical industry and the food industry colouring agents are used widely for the colouring of sugar coatings of e.g. sugar confectionaries, dragees, tablets, pills, gums and granulates. Presently, most colouring agents available for this purpose are based on synthetic dyes, e.g. in the form of food grade lakes which are pigments formed by precipitation and absorption of a dye on an insoluble base or substrate, such as alumina hydrate. A wide range of coating compositions comprising such lakes are available. Presently, propylene glycol-based dispersions are commonly used to incorporate such dyes into solutions used for film-coating of pharmaceutical tablets. It is recognized in the art that propylene glycol has a negative effect on both the processing time and physical properties of the film.

WO 92/11002 discloses a film-forming composition for use in coating tablets and capsules, consisting of powdered pigment particles, a film-forming, water soluble or water dispersible, edible polymer and about 1–30% by weight of water. This composition is described as a wet powder blend and it is manufactured by blending the dry ingredient followed by the addition of water by spraying it onto the blend.

A well-known problem associated with the use of water soluble or dispersible compositions of colouring agents is the tendency of such agents to migrate from one compartment of a food product or a pharmaceutical product to another where the colouring is undesired. This phenomenon is also referred to as "bleeding".

It is therefore particularly desirable to have water soluble or dispersible natural pigment preparations which do not migrate during manufacturing or within the finished product during storage and handling, or come off when handled.

Other problems or shortages associated with known water-miscible or water dispersible natural colouring agents are low stability against light, heating, catalyst and oxygen generated changes of the colour hue and an unsatisfactory covering ability when used for coating purposes. Problems which are frequently encountered with known water dispersible compositions comprising hydrophilic, water-insoluble pigments when using such compositions in acidic media are that the pigments precipitate, separate and accumulate on surfaces and/or change their colour hue.

Thus, it is apparent that water dispersible colouring compositions containing water-insoluble, hydrophilic natural pigments, which are based on aqueous dispersions of the pigment without potentially undesirable additives including surface active substances or propylene glycol, which are suitable for manufacturing of food products as well as pharmaceutical products, which are more stable to degradation, which do not migrate and which are not associated with the above problems have hitherto not been available to the industry.

The advantages obtained with the colouring agents of the present invention in non-powdered form include:

their use give no dusting problems as it is the case with powdered products, in contrast to a powder product they are more readily dispersible in aqueous systems, their manufacturing does not include a drying step which implies that the production costs are lower and that the pigments are not damaged by heat and oxygen, they possess increased dosage performance, they can be provided with a water content and a consistency which is adapted to the particular field of use, e.g. ranging from concentrated pastes to low viscosity products.

In general, the advantages of the compositions according to the invention include:

they do not give rise to migration problems, they do not contain undesirable additives, they do not precipitate, separate and accumulate on surfaces and/or change their colour hue at low pH, i.e. they are what is referred to in the art as "acid-proof"

they make it possible to confer a desired cloudiness or reflection to otherwise clear media in a controlled manner.

SUMMARY OF THE INVENTION

Accordingly, the invention pertains in one aspect to a ready-to-use pigment composition comprising a dispersion of a water-insoluble, hydrophilic natural pigment in the form of bodies of an average size which is at the most 10 $\mu$m, said bodies being dispersed in the absence of a surface active substance in an aqueous phase comprising a hydrocolloid, the composition containing at least 5% by weight of water.

In another aspect the invention provides a ready-to-use water dispersible pigment composition comprising a dispersion of a water-insoluble, hydrophilic natural pigment in the form of bodies of an average size which is at the most 10 $\mu$m, said bodies being dispersed in the absence of a surface active substance in an aqueous phase comprising a hydrocolloid, the composition containing less than 5% by weight of water, subject to the limitation that when the pigment is carmine or spray dried norbixin the hydrocolloid is not gelatin.

In further aspects the invention relates to the use of such a composition in the manufacturing of an edible product whereby the composition is dispersed in the aqueous phase of said food product, including the use in food products wherein the aqueous phase has a pH which is at the most 7, and the use of the above compositions in the manufacturing of an edible product comprising multiple, separated compartments whereby the composition is dispersed in one or more selected compartments, the composition in one compartment essentially not migrating to other compartment.

In a still further aspect, the invention relates to the use of the above compositions in the manufacturing of a pharmaceutical product.

Still further objectives of the invention are to provide an edible product or a pharmaceutical product comprising the above compositions.

The invention also provides a first method of preparing a ready-to-use water dispersible pigment composition, said method comprising preparing a dispersion of a water-insoluble, hydrophilic natural pigment by mixing the pigment in the absence of a surface active substance into an aqueous phase containing a hydrocolloid, to obtain a dispersion containing the pigment in the form of bodies having an average size of at the most 10 $\mu$m, the composition containing at least 5% by weight of water.

In another aspect the invention pertains to a first alternative method of preparing a ready-to-use water dispersible pigment composition, said method comprising the steps of preparing an alkaline aqueous solution comprising a water-in-soluble, hydrophilic natural pigment, preparing an aqueous dispersion or solution of a hydrocolloid, and mixing the alkaline aqueous solution with the aqueous dispersion of a hydrocolloid, and if desired, adjusting the pH to a level which causes the pigment to precipitate, to obtain the composition comprising the pigment in the form of bodies having an average size of at the most 10 $\mu$m, the composition containing at least 5% by weight of water.

In yet another aspect the invention relates to a second alternative method of preparing a ready-to-use water dispersible pigment composition, said method comprising the steps of preparing an alkaline aqueous solution comprising a water-insoluble, hydrophilic natural pigment followed by decreasing the pH to a level which causes the pigment to precipitate, resulting in a dispersion of precipitated pigment, preparing an aqueous dispersion or solution of a hydrocolloid and mixing the dispersion comprising the precipitated pigment with the dispersion or solution of hydrocolloid to obtain the composition comprising the pigment in the form of bodies having an average size of at the most 10 $\mu$m, the composition containing at least 5% by weight of water.

DETAILED DISCLOSURE OF THE INVENTION

The ready-to-use compositions according to the invention comprise or are based upon a dispersion of a water-insoluble, hydrophilic natural pigment. As used herein the term "water-insoluble, hydrophilic" indicates that the pigment in the amounts used herein is water-insoluble or sparingly soluble in aqueous media at about neutral pH or below or at pH levels up till about 9, but soluble in an alkaline aqueous medium such that the pigment will occur as a separate phase in aqueous media at neutral pH or below.

In this context, the term "surface active substance" is used interchangeably with the term "surfactant" and "tenside" and it includes compounds which are generally referred to as anionic, cationic, non-ionic, amphoteric and zwitterionic surfactants. A review of such surface active substances is e.g. given by I Smith, Blackie Academic & Professional, 1991, 169–201. As used herein the term "surface active substance" does not include hydrocolloids as mentioned below. It is to be understood, that the expression "in the absence of a surface active substance" does not exclude the presence of a surfactant in minor amounts which substantially does not impart surface activity.

The natural pigment can be any food grade or pharmaceutically acceptable water-insoluble, hydrophilic colouring matter derived from a natural source. Thus, the pigment may either be in a substantially pure form or it may be contained in the material where it occurs naturally such as a plant or animal material, optionally in combination with a food grade and/or pharmaceutically acceptable carrier. The most widely used natural pigments as defined herein include water-insoluble, hydrophilic carotenoids such as e.g. norbixin, curcumin, porphyrin pigments including chlorophyllin, and carmine.

Carotenoids which have yellow, orange or red colours occurs widely in nature and important sources are plants including grasses, the annatto tree, citrus species, *Capsicum annum, Crocus sativus* flowers and marigold flowers, marine algae, yeast and some animals. Carotenoids or derivatives hereof which are water-insoluble and hydrophilic are useful in the present invention.

A further important class of natural pigments is quininoid pigments of which the most widely used is cochineal carmine which is obtained by aqueous extraction from the insect *Coccus cacti*. Normally, the extract is precipitated as the insoluble aluminium lake known as cochineal carmine which is soluble in alkaline aqueous media but sparingly soluble in aqueous media having pH below about 9.

Further water-insoluble, hydrophilic natural pigments that are useful in the present invention are curcumin, which is the major pigment in turmeric, the coloured oleoresin extract of the Curcuma plant, and water-insoluble hydrophilic porphyrin pigments such as chlorophyllin and pigment based substantially on water soluble salts of derivatives of phaeophytin a or b.

In accordance with the invention the natural pigments in the above compositions are present in the form of bodies of an average size which is at the most 10 $\mu$m. Preferably, the pigment is in the form of bodies having an average size of at the most 5 $\mu$m, preferably at the most 2 $\mu$m and more preferably at the most 1 $\mu$m, e.g. at the most 0.1 $\mu$m or at the most 0.01 $\mu$m. It is contemplated that the ability of the pigment to provide an attractive colour hue and to provide an effective colouring e.g. when the composition is used in coating compositions, is increasing with decreasing size of the pigment bodies. The colour intensity, colour hue and the transparency can be controlled by appropriately selecting the size of the bodies.

In accordance with the invention, the pigment bodies are preferably solid particles such as e.g. solid particles of curcumin, carmine, norbixin and chlorophyllin.

As mentioned above, the natural pigment-containing bodies are dispersed in an aqueous phase comprising a hydrocolloid and the dispersion is provided without the addition of surface active substances such as an emulsifying agent or a surfactant. For the purposes of the present invention suitable hydrocolloids include: an animal or vegetable protein such as gelatin which can be derived from mammals or fish, milk protein or soy protein, an exudate such as gum arabic, tragacanth and other gums such as guar gum, locust bean gum or xanthan gum, agar, alginate, carrageenan, furcelleran, pectin, cereal flours and starches, starch derivatives, microcrystalline cellulose, cellulose derivatives such as carboxymethyl cellulose, dextran, and synthetic hydrocolloids including as an example polyvinylpyrrolidone. Presently preferred hydrocolloids are gelatin and gum arabic. The hydrocolloid can also be a mixture of hydrocolloids.

It is contemplated that the hydrocolloid acts as a protective colloid, that it prevents agglomeration of the pigment bodies and that it provides wetting and dispersing activity.

The hydrocolloid is suitably used in an amount in the range of 1–90% by weight of the natural pigment, such as in the range of 2–80% by weight. In preferred embodiments, the amount of hydrocolloid is in the range of 3–60% by weight such as in the range of 5–50% by weight and e.g the amount of hydrocolloid can be less than 10% by weight of the natural pigment. In other preferred embodiments, the amount of hydrocolloid is more than 100% by weight of the natural pigment, i.e. the ratio between pigment and hydrocolloid can be in the range of 1:1 to 1:10000, such as in the range-of 1:10 to 1:5000 or in the range of 1:100 to 1:1000.

The amount of pigment may also be calculated on the composition. Thus, the amount of hydrocolloid is preferably in the range of 1–50% by weight of the composition, preferably in the range of 5–40% by weight, such as in the range of 10–25% by weight.

In accordance with the invention, the composition may preferably contain at least 5% by weight of water such as in excess of 10% by weight. One advantage of such a composition is the possibility of providing it with a water content within a wide range whereby the composition can be adapted to particular customer demands. A composition containing at least 5% by weight of water having a low content of water will appear as a powder or a viscous paste. Depending on the natural pigment, a composition having a water content in the range of 5–40% by weight will typically appear as a powder, a paste, a gel or a viscous liquid. With an increasing water content above this level, the consistency of the composition will acquire an increasingly lower viscosity and become liquid. It is contemplated that a concentrated pasty composition will be advantageous from a user point of view, since it can easily be transported and stored and furthermore, the natural pigment will be protected well against light and oxidation in such a concentrate. It is evident that a concentrated composition according to the invention with an initial water content of at least 5% by weight can be diluted with water to any desired pigment concentration.

In other useful embodiments of the invention the above compositions contain less than 5% by weight of water, subject to the limitation that when the pigment is carmine or spray dried norbixin the hydrocolloid is not gelatin.

The selection of a suitable amount of the natural pigment in the composition according to the invention depends on the particular type of pigment and the particular intended application for the composition and a wide range of the amount of pigment is therefore contemplated such as a range of 0.5–90% by weight of the dispersion, although amounts in excess of this range is envisaged. In preferred embodiments, the amount of pigment is in the range of 1–50% by weight, and may more preferably be in the range of 5–40% by weight. Based on the dispersed phase a useful amount is in the range of 10 to 30% by weight, including about 20% by weight of the dispersion.

In specific embodiments of the invention the pigment is in the form of pigment particles obtained by precipitation caused by acidification of an alkaline solution of the pigment.

In accordance with the invention, the aqueous phase of the composition can as a further component comprise a carbohydrate or a sugar alcohol or a mixture hereof. The carbohydrate is preferably selected from a monosaccharide, a disaccharide or an oligosaccharide including as examples glucose, lactose, fructose, sucrose. The sugar alcohol can e.g. be selected from sorbitol, mannitol, dulcitol, adonitol or sorbitol. The amount of the sugar alcohol is preferably in the range of 0–95% by weight of the dispersion, such as 5–50% by weight including the range of 10–30% by weight.

In useful embodiments, the composition according to the invention is a coating composition comprising the above dispersion of a water-insoluble, hydrophilic natural pigment and at least one further ingredient which is normally used in a composition for colouring coating layers of e.g. a tablet, a dragee, a pill or a capsule. Such further ingredients can be selected from additional sugar to provide a syrup, a plasticizing agent such as propylene glycol, a film coating resin, a stabilizing agent, a further colouring agent such as $CaCO_3$ or titanium dioxide, or a lower alcohol. The composition may also be a composition intended for decoration purposes such as a glazing composition or a "printing" composition.

The composition according to the invention is, as it is mentioned above, useful as a colouring agent for food products. Any food product comprising an aqueous phase wherein the composition is dispersible can be coloured. A large number of food products have an aqueous phase with a pH below 7 and this acidic environment will in many cases render a pigment as such unstable and the pigment will tend to precipitate resulting in a change of the colour hue. This is e.g. observed in products such as acidified milk products.

The compositions of the present invention are specifically useful in an acidic food product since the compositions are acid-proof and do not precipitate.

In another useful embodiment of the invention the composition is suitable for colouring of liquid food products including soft drinks, carbonated beverage products and milk products.

An interesting application of the composition according to the invention is the colouring of edible products being manufactured by extrusion, e.g. edible film for containing a food product such as a meat product. A typical example hereof is collagen films used as casings for sausage products. An effective amount of the colouring composition is added to the aqueous mixture to be extruded or casted and the resulting edible film will contain the colour pigments. It has been found that the natural pigments when incorporated in such extruded edible films in contrast to known food colours do not migrate into the contained food product and furthermore, the pigment is not released into water in which the products are cooked.

Other examples of extruded products where the pigment compositions according to the invention are useful include breakfast cereals, cakes, bread, snacks, confectionary products, breadings, crisps and grains. It has been found that the fact that the compositions do not contain any lipids or surface active substances make them particularly useful in the manufacturing of expanded products made by an extrusion process, since the expansion in such processes is lower when lipids and/or surface active substances are added to the extrusion mixture.

A further advantageous use of the compositions is the colouring of confectionary products including as examples candies, acid drops and jelly products since the pigments in the compositions according to the invention are acid stable.

Several food products such as e.g. soft drinks, juices, soups and sauces are manufactured as initially liquid products which are subsequently dehydrated to a dry, storage stable product typically having a water content of at the most 10% by weight. The compositions according to the invention are also useful for the colouring of such products in that the colouring of the products after rehydration will substantially be of the same strength and hue as the starting liquid food product.

As it is mentioned above, it is a well known problem in the food industry that colouring agents used in food products tend to migrate within the food product or into the environment of the product. This phenomenon is also in the art referred to as "bleeding". This problem is particularly troublesome if it occurs in food products which comprise multiple, separated compartments or layers where the colouring agent is not added to all of such compartments, but only to one or more selected compartments. A colouring agent which do not migrate in such products are therefore highly desirable in the industry. It has been found that the pigments of the compositions according to the invention are retained in the compartment(s) to which they have been added and do not migrate into adjacent non-coloured compartments.

One typical example of such a compartmentalized or layered food product is dessert products, which optionally are acidulated, comprising at least one layer of fruit filling to which a colouring agent is added, and one or more layers of other ingredients also having an aqueous phase but to which a colouring agent is not added. Another example of such a product is a layered cake. It is evident that migration of colouring agent into the non-coloured layers result in a highly unacceptable appearance of these layered products. As it is shown in the below examples, the compositions according to the invention can be used in such products without giving rise to "bleeding" problems. A further example of a product where it is advantageous to avoid migration of pigments is a cereal breakfast product to be eaten with milk.

Avoidance of pigment migration is also critical in connection with edible products comprising a surface decoration layer in which a colouring agent is dispersed. Clearly, it is undesirable if the added pigment migrates from the decoration layer into the subjacent product layer. Typical examples of surface decorated products are meat products such as surimi and other delicatessen products where the decoration e.g. may be in the form of a water-based gel which is coloured with the pigment composition while liquid and subsequently applied on the product to solidify. Other examples of surface decorated products are bakery product having sugar icing (glazing) on top or coloured decoration particles. When added to such decoration layers or particles, the pigments in the compositions according to the invention do not migrate from the layers or particles.

Dragees constitute a particular type of edible multilayered products where one or more coating layers typically consisting of sugar are applied onto a center of an edible ingredient. Examples of such centers to be coated include chewing gum, sugar granulates, sugar tablets and chocolate. Colouring of such edible centers is typically carried out in one or more panning steps where the centers are coated with a sugar syrup containing the colouring agent. Normally, it is required to apply several coating layers to obtain a sufficient covering with colour. With known water soluble or dispersible colouring agents based on lakes it is frequently required to apply 20 coating layers or more. It has been found that the compositions according to the invention are highly suitable for such coating purposes and that dragees with a sufficient colouring can be obtained by applying less than 20 layers, such as 2–15 layers. Furthermore, it has been found that the natural pigments of the compositions as contained in coating layers do not come off on fingers on handling or on mucosal surfaces when the dragees are consumed.

A highly attractive characteristic of the compositions according to the invention is that they are useful as colouring agents in the manufacturing of a pharmaceutical product. Thus, the compositions can be used for colouring of pharmaceutical products comprising multiple, separated compartments essentially in the same manner and with the same advantages as described above for compartmentalized food products. In particular, the compositions according to the invention are useful for colouring of compositions for conventional film-coating of tablet, pills or granules containing pharmaceutically active substances.

For such coating purposes the water dispersible composition according to the invention is typically added to a sugar syrup suspension, e.g. using sucrose. The solids content of such a coating syrup is normally in the range of 60–80% by weight. The amount of the natural pigment composition which is added to the coating syrup is generally in the range of ½-50% by weight of the syrup. The thus coloured coating mixture may contain further components such as stabilizers, preservatives, viscosity modifying agents and plasticizers.

The pharmaceutical centers are coated repeatedly in a conventional panning process and the number of repeated coatings required depends on the particular pigment and the desired appearance of the finished product. However, with the composition according to the invention, relatively few coating layers are required to obtain an attractive colouring. Thus, less than 20 layers is normally required and in most cases, 5–15 layers will suffice.

In addition to the above applications of the compositions, it is contemplated that they are also useful for colouring of pharmaceutical products in liquid form such as solutions, suspensions or dispersion having an aqueous phase.

As mentioned above, the present invention provides in one aspect a first method of preparing the ready-to-use water dispersible pigment compositions according to the invention.

In a first step of this method a dispersion of a water-insoluble hydrophilic natural pigment is prepared by mixing the pigment into an aqueous phase. This mixing step is carried out without the addition of surface active substances such as emulsifying compounds, but in the presence of a hydrocolloid of a type and in amounts as mentioned above. As also mentioned above the invention pertains to a first and second alternative method of preparing the ready-to-use water dispersible pigment compositions according to the invention.

The mixing steps in the above methods can be carried out by any conventional mixing or blending technique known in the art. Optionally, the mixing can be followed by comminution to obtain discrete pigment bodies having a size of at the most 10 $\mu$m. However, it may be advantageous to continue the comminution until the pigment is in the form of bodies having an average size of at the most 5 $\mu$m, preferably at the most 2 $\mu$m and more preferably at the most 1 $\mu$m. It may also be advantageous to let the comminution proceed until an average body size of at the most 0.1 $\mu$m such as at the most 0.01 $\mu$m is achieved The above comminution step may be repeated one or more times in order to obtain the required body size.

Applicable comminution techniques include milling and homogenization as it is described in the below examples.

In useful embodiments of the invention the pigment is in the form of particles obtained by precipitation of the pigment caused by acidifying an alkaline solution of the pigment.

In useful embodiments of the methods according to the invention, the amount of hydrocolloid is less than 10% by weight of the pigment.

The steps of dispersing the pigment can, if desired, be carried out in at least two steps in which an additional amount of hydrocolloid may be added in the second and/or any subsequent step.

It will be understood that the methods of the invention may also comprise the preparation of a pigment dispersion in which a mixture of two or more water-insoluble, hydrophilic natural pigments is used. In this manner pigment compositions having a particular attractive colour tone can be provided as a result of the combination of two or more pigments having differing colours.

As also mentioned above, the methods may in accordance with the invention comprise the addition of a carbohydrate to the aqueous phase either before or after the mixing or comminution or they may comprise the incorporation into the dispersion of the water-insoluble, hydrophilic natural pigment of at least one further ingredient. Such further ingredients may e.g. be selected from antioxidants, stabilizing agents, plasticizers, viscosity modifying agents, alcohols, resins and preservative agents.

In useful embodiments of the invention the above methods comprise a further step of drying to obtain a composition containing less than 5% by weight of water, subject to the limitation that when the pigment is carmine or spray dried norbixin, the hydrocolloid is not gelatin.

The present invention is further illustrated by the following non-limiting examples:

EXAMPLE 1
Preparation of a Carmine Composition 7.9 kg gelatin (dry weight) was added slowly to 17.3 kg demineralised water at a temperature of about 65° C. with stirring until the gelatin had dissolved. 14.2 kg of sucrose was added with agitation until the sugar was dissolved. 10.5 kg of carmine lake powder (50–52% carmine) was added to the above solution under agitation using a mechanical stirrer until a homogeneous mixture was obtained.

The mixture was milled using a suitable equipment until a stable pigment dispersion was obtained. The milled product was heated under gentle agitation to about 75° C. and kept at this temperature for about 10 minutes. The resulting pigment composition had a water content of about 35% by weight and a pigment content of about 10% by weight.

Working Instruction 1
Preparation of Carmine Composition Using Gum Arabic as Hydrocolloid The composition is prepared using essentially the same method and ingredients as described in Example 1 substituting 7.9 kg gelatin with 10.5 kg gum arabic (dry weight) and reducing the amount of sugar to 11.6 kg.

EXAMPLE 2
Preparation a Carmine Composition with Dispersion of Carmine in Two Steps 1.0 kg of gelatin (dry weight) was added slowly to 16.0 kg demineralised water at a temperature of about 65° C. with agitation until the gelatin was dissolved. 15.5 kg of sucrose was added under agitation until the sugar was dissolved. 10.5 kg of carmine was added to the above mixture under agitation using a mechanical stirrer. Mixing was continued until a homogeneous mixture was obtained. The mixture was milled using a suitable mill until a stable dispersion of the pigment was obtained. The milled product was heated under gentle agitation to about 70° C., 7.0 kg of gelatine was added and dissolved using agitation. The temperature was kept at this temperature for about 10 minutes. The resulting composition has a water content of about 32% by weight.

EXAMPLE 3
Preparation of a Norbixin Composition

A gelatin-sugar solution was prepared by slowly adding 2.0 kg gelatin (dry weight) to 4.4 kg of demineralised water at a temperature of about 65° C. with agitation until the gelatin was dissolved. 3.6 kg sucrose was added with agitation until the sugar was dissolved. 0.39 kg pigment A-1400-WS (4.8% alkaline aqueous solution of annatto) was added to 9.6 kg the above mixture under agitation using a mechanical stirrer. Mixing was continued until a homogeneous mixture was obtained. The pH of the mixture was about 5.6. The resulting composition has a water content of about 46% by weight.

EXAMPLE 4
Preparation of a Chlorophyllin Composition 100 g chlorophyllin powder was dissolved in 300 g demineralised water and the pH of the solution was decreased to about 4–5 with 25 g citric acid. 150 g gelatin (dry weight and 425 g sucrose was added and dissolved by increasing the temperature of the medium to about 65° C. with agitation until a homogeneous mixture was obtained.

The mixture was milled until the required pigment size was obtained. The milled product was heated under gentle agitation to about 75° C. and kept at this temperature for about 10 minutes. The resulting pigment composition had a water content of about 30°% by weight.

EXAMPLE 5
Comparative Study of Migration in an Acidulated Dessert Coloured with Pigment Composition According to the Invention and Reference Colouring Agents Mashed apple was mixed with the below amount of colouring agents and 25 ml glass containers were filled half with the mixtures, the remaining half of the containers were filled with yogurt. The container were kept at 5° C. and the migration of the colour into the yogurt layer in cm was recorded after 4, 7, 11 and 28 days.

The reference colouring agent was a product of Chr. Hansen A/S, Hørsholm, Denmark. The following agents were tested (dosages in g colouring agent/g mashed apple):

CO-820-WS-AP: carmine acid dissolved in propylene glycol, citric acid and water (0.150)

Carmine composition of Example 1 (0.052),

TABLE 5.1

Migration of test compositions and reference colouring agents in cm

| | Days | | |
|---|---|---|---|
| | 4 | 7 | 11 |
| Carmine, reference | 1 | 1.8 | 1.8 |
| Carmine, test | 0 | 0 | 0 |

These results clearly shows that migration did not occur with the natural pigment composition according to the invention, whereas the reference product containing the corresponding pigments in solution migrated to a significant extent.

EXAMPLE 6
Coating of Confectionary Using Coating Syrups Containing Natural Pigment Compositions A coating syrup was prepared from 3.5 kg sucrose and 1.5 kg water by mixing and heating to 80° C. under agitation with a propel stirrer. The syrup was cooled to 50° C. and 270 g of a natural pigment composition according to the invention containing about 5% of pigment was added to the syrup.

A coloured coating syrup containing a pigment composition with carmine was prepared in this manner. The concentration of the natural pigment in the syrup was about 0.4% of the syrup dry matter.

4–5 kg confectionary centers with a diameter of 17 mm and with a sugar coating containing $TiO_2$ were used to test the colouring ability of the coating syrup.

In the experiment, a satisfactory colour of the resulting dragees was obtained even with 3–4 layers of coloured syrup and a strong and dark colour was obtained after 10 layers of coating.

The experiment illustrated that the natural pigment composition dispersed very well without the use of a-high speed mixer.

The colouring ability was high in that good colouring was seen after only 3–4 layers without the addition of gum arabic which is often used in coating syrups to enhance the adherence of the colouring agent. It was observed that no colouring of teeth, mouth or hands occurred on eating the coloured dragees.

EXAMPLE 7
The Performance at Low pH of a Carmine Composition According to the Invention (Test-Carmine)

A problem which is encountered with known colouring agents containing carmine lake is that they are not suitable for use in acid products since the lake at low pH is dissociated into free carminic acid whereby the colour hue changes from carmine red to orange red. Additionally, the low pH generated degradation of the lake may include a precipitation of the chelated carminic acid.

The Test-Carmine product was therefore tested for possible acid stability by adding it to the soft drink medium as described below. A concentrated soft drink medium with the following composition was initially prepared:

| | |
|---|---|
| Sucrose | 430.0 g |
| Na-benzoate, food grade | 0.7 g |
| K-sorbate, food grade | 0.9 g |
| Ascorbic acid | 0.1 g |
| Citric acid monohydrate, food grade | 8.6 g |
| Demineralised water, | ad 1000.0 g |

Subsequently the concentrated medium was diluted 1:4 with demineralised water resulting in a soft drink medium having a pH of 3.0±0.2. 200 ppm pigment composition as prepared in Example 1 was added as test sample to the diluted soft drink medium. As references were used equivalent pigment concentrations of the above colouring agent CO-820-WS-AP (Example 5) which contain carminic acid in propylene glycol and citric acid and CC-500-WS, an alkaline solution of carmine.

After addition of the Test-Carmine and the reference colouring agent, the colour hue of the soft drink with Test-Carmine was carmine red as desired whereas the soft drink with the reference product CO-820-WS-AP became orange and the reference product CC-500-WS precipitated. No precipitation of carminic acid was observed in the Test-Carmine sample. After 50 days, the carmine red colour hue was retained in the sample with Test-Carmine.

It was also observed that the addition of the Test-Carmine composition resulted in an attractive cloudiness (which is not due to precipitation) of the soft drink in contrast to the reference sample which remained transparent.

EXAMPLE 8

The Performance of Pigment Compositions in Soft Drink

10% by weight of pigment compositions of carmine and chlorophyllin as prepared in Examples 1 and 4, respectively (Test-Carmine and Test-Chlorophyllin) were added as test samples to the diluted soft drink medium as prepared in Example 7. The following colouring agents containing the corresponding pigments were added to the soft drink medium as reference samples:

CC-500-WS, 5% carmine in alkaline solution,

C-10,000-WS-AP, chlorophyllin in polysorbate and propylene glycol, $L^*a^*b^*$ values were measured using a Minolta Tristimulus CT-210 equipped with a D65 lamp in a 1 cm cuvette. The measurements were made after dissolution/dispersing of the colours and after storage for 8 weeks in the light and dark, respectively. ΔE expresses the difference in colour parameters. The results are summarized in the below table:

TABLE 8.1

Appearance of soft drink medium and colour parameters after storage and exposure to light

| | Appearance | | Colour parameters | | |
|---|---|---|---|---|---|
| | Initial | After 1 week | ΔE | Δ hue angle | Test condition |
| Test-Carmine | Cloudy | Cloudy | 21 | | Daylight 8 weeks |
| CC-500-WS | Transparent | Precipitated | 60 | | |
| Test-Chlorophyllin | Cloudy | Cloudy | 2.8 | 2.6 | 1.5 hours in Suntester CPS |
| C-10,000-WS-AP | Transparent | Cloudy/precipitated | 6.4 | 12.1 | 600 W/m², Xenon |

These results illustrate that the compositions according to the invention have a high stability as compared to the reference colouring agents. Furthermore, the water dispersible Compositions of the invention confer to the soft drink medium a cloudy appearance whereas the reference soft drink samples remained transparent. A cloudy appearance of a soft drink is a highly desirable characteristic of a coloured soft drink.

EXAMPLE 9

The Performance at Low pH of Norbixin Composition According to the Invention (Test-Norbixin)

About 1 ml of the norbixin composition obtained in Example 3 and a reference A-320-WS (1.1% alkaline aqueous solution of annatto) were added to 100 ml demineralised water and the above soft drink medium, respectively. The following was observed:

TABLE 9.1

Performance of norbixin composition in soft drink and demineralised water

| | Demineralised water | Soft drink medium |
|---|---|---|
| Test-Norbixin | Cloudy | Clear yellow/orange solution |
| A-320-WS | Clear orange/yellow solution | Precipitation |

The four samples were stored at room temperature in a dark place for 15 month. The reference sample was unchanged in the soft drink solution whereas the colour had disappeared from the reference sample in demineralised water. The Test-Norbixin was unchanged both in the soft drink medium and in the demineralised water sample.

The above shows that with the compositions of the present invention it is also possible to obtain transparent solutions at acidic pH and that they are stable in acidic media.

EXAMPLE 10

The Performance of Chlorophyllin in Soft Drink Concentrate 200 ppm chlorophyllin composition as prepared in Example 4 was used as colouring agent in the concentrated soft drink medium described in Example 7. A reference sample was coloured using the above described colour C-10,000-WS-AP in the same chlorophyllin concentration. The following results were obtained after 1 and 4 weeks of storage:

TABLE 10.1

Appearance of concentrated soft drink medium

| Colouring agent | 1 week | 4 weeks |
|---|---|---|
| Test-Chlorophyllin | No ring formation | No ring formation |
| C-10,000-WS-AP | Ring formation | Ring formation |

The above results show that with regard to ring formation the compositions according to the invention are superior to the equivalent water-soluble composition.

What is claimed is:

1. A ready-to-use water dispersible pigment composition that contains in excess of 10% by weight of water, the composition comprising a dispersion of a water-insoluble hydrophilic natural pigment in the form of bodies of an average size which is at the most 10 µm, said bodies being dispersed in the absence of a surface active substance in an aqueous phase comprising a hydrocolloid, the composition, when it is added to a food product or a pharmaceutical product comprising multiple, separated compartments, whereby the composition is dispersed in one or more selected compartments, essentially does not migrate from said compartment(s) where it is dispersed into other compartments.

2. A composition according to claim 1 wherein the natural pigment is a pigment that is generally insoluble in aqueous media at about neutral pH or below but soluble in aqueous media at pH values in the alkaline range.

3. A composition according to claim 2 wherein the pigment is selected from the group consisting of a porphyrin pigment, carmine, curcumin and a carotenoid.

4. A composition according to claim 3 wherein the pigment is in the form of particles obtained by precipitation of the pigment caused by acidifying an alkaline solution of the pigment.

5. A composition according to claim 1 wherein the aqueous phase comprises a carbohydrate.

6. A composition according to claim 1 wherein the hydrocolloid is selected from a protein, a polysaccharide and a gum.

7. An edible product comprising a composition according to claim 1.

8. An edible product according to claim 7, comprising multiple, separated compartments such that the composition is dispersed in one or more selected compartments, and the composition in one compartment essentially not migrating to other compartments.

9. A pharmaceutical product comprising a composition according to claim 1.

10. A pharmaceutical product according to claim 9, comprising multiple, separated compartments such that the composition is dispersed in one or more selected compartments, and the composition in one compartment essentially not migrating to other compartments.

11. A method of preparing a ready-to-use water dispersible pigment composition according to claim 1, said method comprising preparing a dispersion of a water-insoluble, hydrophilic natural pigment by mixing the pigment in the absence of a surface active substance into an aqueous phase containing a hydrocolloid, to obtain a dispersion comprising the pigment in the form of bodies having an average size of at the most 10 µm, the composition containing at least 10% by weight water.

12. A method according to claim 11, which comprises the further step of drying the dispersion to obtain a composition containing less than 5% by weight of water, subject to the limitation that, when the pigment is carmine or spray-dried norbixin, the hydrocolloid is not gelatin.

13. A method according to claim 11 wherein the solid pigment is in the form of particles obtained by precipitation of the pigment caused by acidifying an alkaline solution of the pigment.

14. A method according to claim 11 wherein the amount of hydrocolloid is less than 10% by weight calculated on the pigment.

15. A method according to claim 11 which comprises a further step wherein an additional amount of hydrocolloid is added.

16. A method according to claim 11 wherein a carbohydrate is added to the aqueous phase.

17. A ready-to-use water dispersible pigment composition comprising a dispersion of a water-insoluble, hydrophilic natural pigment in the form of bodies of an average size which is at the most 10 μm, said bodies being dispersed in the absence of a surface active substance in an aqueous phase comprising a hydrocolloid, the composition containing less than 5% by weight of water, subject to the limitation that when the pigment is carmine or spray dried norbixin the hydrocolloid is not gelatin, said composition, when it is added to a food product or a pharmaceutical product comprising multiple, separated compartments, whereby the composition is dispersed in one or more selected compartments, essentially does not migrate from said compartment(s) where it is dispersed into other compartments.

18. A composition according to claim 17 wherein the composition is dispersed in an aqueous phase of said edible food product.

19. A composition according to claim 17 wherein said composition is a pharmaceutical product.

20. A ready-to-use water-dispersible composition comprising a dispersion of a hydrophilic natural pigment in the form of bodies of an average size which is at the most 10 μm, said bodies being dispersed in the absence of a surface active substance in an aqueous phase comprising a hydrocolloid, the composition containing in excess of 10% by weight of water, in the manufacturing of an edible product whereby the composition is dispersed in an aqueous phase of said edible food product.

21. A composition according to claim 20 wherein the aqueous phase has a pH which is at the most 7.

22. A ready-to-use water-dispersible composition comprising a dispersion of a hydrophilic natural pigment in the form of bodies of an average size which is at the most 10 μm, said bodies being dispersed in the absence of a surface active substance in an aqueous phase comprising a hydrocolloid, the composition containing in excess of 10% by weight of water, in the manufacturing of a pharmaceutical product.

23. A method of preparing a ready-to-use water dispersible pigment composition, said method comprising the steps of:
  i) preparing an alkaline aqueous solution comprising a water-insoluble, hydrophilic natural pigment,
  ii) preparing an aqueous dispersion or solution of a hydrocolloid,
  iii) mixing the alkaline aqueous solution with the aqueous dispersion or solution of a hydrocolloid and
  iv) if desired, adjusting the pH to a level which causes the pigment to precipitate, to obtain the composition comprising the pigment in the form of a dispersion of pigment bodies having an average size of at the most 10 μm, the composition containing at least 10% by weight water.

24. A method according to claim 23, which comprises the further step of drying the composition of pigment bodies to obtain a composition containing less than 5% by weight of water, subject to the limitation that, when the pigment is carmine or spray-dried norbixin, the hydrocolloid is not gelatin.

25. A method according to claim 23 wherein the aqueous solution of step i) and/or the dispersion or solution of step ii) comprises a carbohydrate.

26. A method of preparing a ready-to-use water dispersible pigment composition, said method comprising the steps of:
  i) preparing an alkaline aqueous solution comprising a water-insoluble, hydrophilic natural pigment followed by decreasing the pH to a level which causes the pigment to precipitate, resulting in a dispersion of precipitated pigment,
  ii) preparing an aqueous dispersion or solution of a hydrocolloid,
  iii) mixing the dispersion comprising the precipitated pigment of step i) and the dispersion or solution of a hydrocolloid of step ii), to obtain the composition comprising the pigment in the form of a dispersion of pigment bodies having an average size of at the most 10 μm, the composition containing at least 10% by weight water.

27. A method according to claim 26, which comprises the further step of drying the composition of pigment bodies to obtain a composition containing less than 5% by weight of water, subject to the limitation that, when the pigment is carmine or spray-dried norbixin, the hydrocolloid is not gelatin.

28. A method according to claim 26 wherein the dispersion comprising the precipitated pigment of step i) and the dispersion or solution of step ii) comprises a carbohydrate.

* * * * *